United States Patent [19]

Novick

[11] Patent Number: 4,966,462

[45] Date of Patent: Oct. 30, 1990

[54] SERIES CELL LIGHT EXTINCTION MONITOR

[75] Inventor: Vincent J. Novick, Downers Grove, Ill.

[73] Assignee: The United States of America as represented by the United States Department of Energy, Washington, D.C.

[21] Appl. No.: 310,128

[22] Filed: Feb. 15, 1989

[51] Int. Cl.$^5$ ............... G01N 21/05; G01N 15/06; G01N 21/59

[52] U.S. Cl. .................................. 356/437; 356/442

[58] Field of Search ............ 356/335, 436, 437, 438, 356/439, 440, 441, 442

[56] References Cited

U.S. PATENT DOCUMENTS

| | | |
|---|---|---|
| 3,700,333 | 10/1972 | Charlson et al. |
| 3,820,897 | 6/1974 | Roess ................................. 356/301 |
| 3,825,345 | 7/1974 | Lorenz . |
| 3,869,208 | 3/1975 | Lorenz ............................. 250/227 |
| 3,979,596 | 9/1976 | Shaw et al. ...................... 250/575 |
| 4,018,534 | 4/1977 | Thorn et al. ..................... 250/575 |
| 4,200,399 | 4/1980 | Kimble et al. ................... 356/437 |
| 4,247,783 | 1/1981 | Berber et al. .................... 250/574 |
| 4,687,337 | 8/1987 | Stewart et al. .................. 356/437 |

Primary Examiner—Vincent P. McGraw
Attorney, Agent, or Firm—Mark P. Dvorscak; Paul A. Gottlieb; William R. Moser

[57] ABSTRACT

A method and apparatus for using the light extinction measurements from two or more light cells positioned along a gasflow chamber in which the gas volumetric rate is known to determine particle number concentration and mass concentration of an aerosol independent of extinction coefficient and to determine estimates for particle size and mass concentrations. The invention is independent of particle size. This invention has application to measurements made during a severe nuclear reactor fuel damage test.

14 Claims, 11 Drawing Sheets

Note: All particle diameters are diameter of average mass ($\bar{d}_m$)

Note: All particle diameters are diameter of average mass ($\bar{d}_m$)

FIG. 10

SERIES CELL LIGHT EXTINCTION MONITOR

CONTRACTUAL ORIGIN OF THE INVENTION

The United States Government has rights in this invention pursuant to Contract No. DE-AC07-76ID01570 between the United States Department of Energy and EG&G Idaho, Inc.

BACKGROUND OF THE INVENTION

Light extinction measurements have been used since the late 1800's to quantify aerosol characteristics such as visual range, number concentration and mass concentration These measurement techniques, first developed by Tyndall and Lord Rayleigh, have improved to the point where light extinction is routinely used to determine compliance with the Environmental Protection Agency Clean Air Act requirements.

Light extinction is given by the basic form of the Lambert-Beer law $$I/I_O = \exp(-\sigma L) \qquad (1)$$

where
- $I$ = Transmitted light intensity measured through the aerosol
- $I_O$ = Transmitted light intensity measured without the aerosol
- $\sigma$ = extinction coefficient of the aerosol (cm$^{-1}$)
- $L$ = path length of the light beam through aerosol (cm).

For a monodisperse aerosol containing N particles per cubic centimeter $$\sigma = (N\pi QD^2)/4 \qquad (2)$$

where
- $D$ = geometric particle diameter (cm)
- $Q$ = extinction coefficient of the particle
- $N$ = particle number concentration (cm$^{-3}$)

Aerosol characteristics, i.e. visual range, number or mass concentration, cannot be explicitly calculated from extinction data because usually two or more of the parameters in equation (2) are unknown. Therefore, assumptions, estimations, and correlations must be employed to infer aerosol characteristics from light extinction measurements. As described in "On the Generality of Correlation of Atmospheric Aerosol Mass Concentration and Light Scatter" by R. J. Charlson, N. C. Alquist, and H. Horvath, *Atmospheric Environment*, 2:455–464 (1968), these approximations work reasonably well for a well characterized, stable system such as ambient atmospheric aerosol. The approximations are not valid for a less stable system such as stack emissions, due to instabilities with respect to size distribution and aerosol composition. For these types of systems, light extinction measurements can only be valid on a case by case basis after the specific aerosol has been characterized, as noted by M. J. Pilat and D. S. Ensor in "Plume Opacity and Particulate Mass Concentration" *Atmospheric Environment*, 4:162–173 (1970).

For aerosols such as those released by severe fuel damage to nuclear reactor fuel, the aerosol composition is not well known, much less well characterized, and the aerosol release is necessarily transient. In such a case, conventional light extinction measurements cannot be used to determine number concentration or mass concentration without assuming values for the particle size and extinction coefficients.

Accordingly, it is an object of the present invention to provide a light extinction apparatus and method to determine the number concentration of an aerosol without assuming values for the particle size and extinction coefficient.

It is a further object of this invention to determine number concentration of an aerosol in an cost effective accurate manner.

It is a still further object of this invention to determine estimates for particle size, aerosol mass concentration, and aerosol mass flow rate in a light extinction apparatus.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

This invention is a method and apparatus for using the light extinction measurements from two or more light cells positioned along a flow chamber in which the gas volumetric flow rate is known to determine particle number concentration and mass concentration of an aerosol independent of extinction coefficient and to determine estimates for particle size and mass concentrations. The invention is independent of particle size.

BRIEF DESCRIPTION OF THE DRAWINGS

FIG. 10 is a graph plotting aerosol concentration verses time.

DETAILED DESCRIPTION OF THE INVENTION

The present invention, the series cell aerosol monitor, advances from the combination of light scattering theory and coagulation theory. The embodiment described herein was designed to measure the light extinction due to aerosols released during severe fuel damage experiments conducted at the Power Burst Facility (PBF) nuclear reactor located at the Idaho National Engineering Laboratory (INEL). This embodiment was used specifically to provide information correlating the generation and release of aerosols to various events occurring in the reactor core during the PBF Severe Fuel Damage (SFD) 1-4 test and to provide an estimate of the particle number concentration as a function of time. However, the invention can be adapted for other uses such as monitoring stack emissions for environmental compliance or safety controls.

Figure 1:
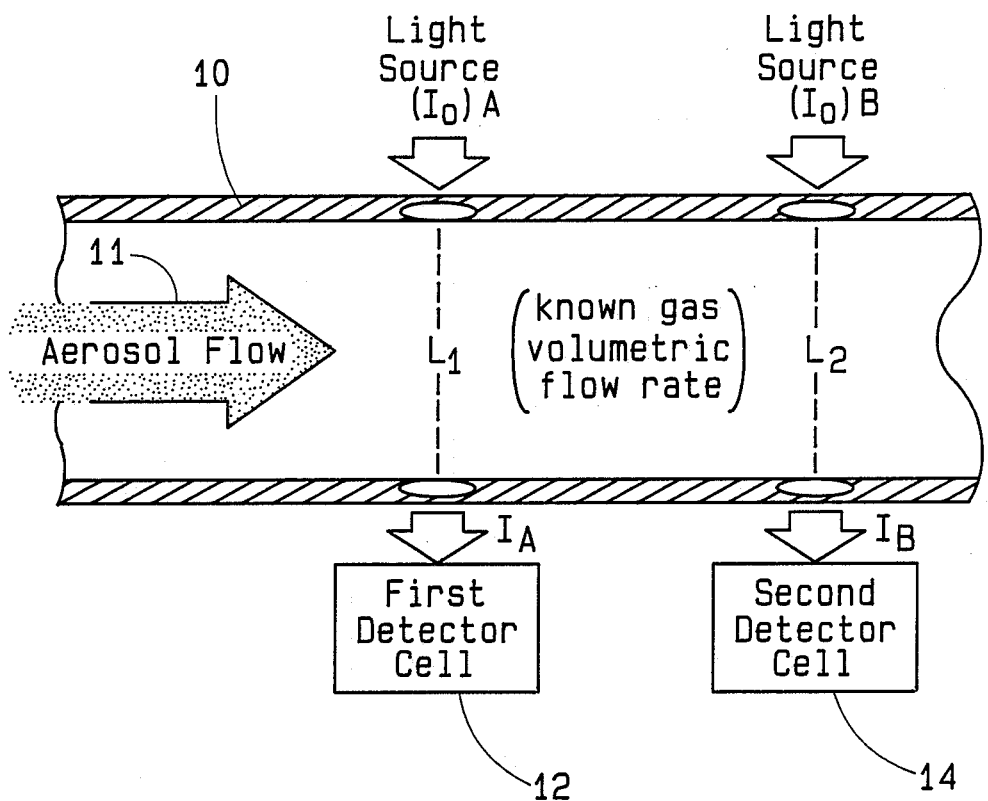
FIG. 1 depicts a general schematic of the present invention.

Referring to FIG. 1, there is illustrated a general schematic of the present invention. The present embodiment uses two light cells although more than two cells could be used to provide additional accuracy or redundancy controls. Both cells were identical except for the difference in path length across the gasflow chamber. This embodiment, using detectors with different optical path lengths, provides a wide dynamic range of extinction measurement. In other usages, this consideration may not be important and the cells could be designed with equal path lengths or path lengths that are adapted to the emission stack geometry.

A gasflow chamber 10 conveys an aerosol flow 11 that passes a first light extinction cell 12 of known path length and then a second light extinction cell 14 of known path length separated from the first cell. The present invention assumes that the gas volumetric flow rate is known or can be calculated or measured by conventional methods or equipment, as is well known in the art. First light extinction cell 12 has an optical path length $L_1$ and second light extinction cell has optical path length $L_2$.

Equations (1) and (2), above, describe the light extinction due to a monodisperse aerosol distribution. Based upon the work reported in R. Dennis, in *Handbook on Aerosols*, Technical Information Center, Office of Public Affairs, U.S. Energy Research and Development Administration, Oak Ridge, Tenn., pp. 66–92 (1976), it can be shown that the equations can be modified for a polydisperse aerosol by keeping N as the total number of particles, L as the path length, and identifying D as some moment of particle size describing the distribution. The preferred moment is chosen by considering a log-normal number distribution of aerosols undergoing coagulation. First, the coagulation process does not change the total mass of aerosol passing through the cells. Second, size parameters based on particle number are located near the mode of the distribution. Size parameters based on number are located near the mode of the distribution. The coagulation process removes smaller particles and adds larger ones to the distribution. The differences in mean number diameters and modes between the initial and final distributions are significant. However, a size parameter based on mass is located on the tail of the distribution, far from the mode. Therefore, the difference in mass diameters between the initial and final distributions, because of coagulation, is much less significant. Third, the diameter of average mass allows immediate determinations of total mass. For these reasons, $D_m$, will be the moment chosen to describe the particle size of the aerosol distribution.

For a polydisperse aerosol, the extinction coefficient, Q, must be written as an integral over particle size, particle extinction coefficient, and size distribution.

If the value of this integral is designated by $Q_{ext}$, the following equation describes the light extinction for each cell $$I_A/(I_O)_A = \exp[-N_A \pi (D_m)_A^2 L_1 (Q_{ext})_A/4] \quad (3a)$$

$$I_B/(I_O)_B = \exp[-N_B \pi (D_m)_B^2 L_2 (Q_{ext})_B/4] \quad (3b)$$

The designations 'A' and 'B' denote the first cell 12 and the second cell 14, respectively. Since the cells are in series, the following assumptions can be made for short transit times:

$$(Q_{ext})_A = (Q_{ext})_B \quad (1)$$

$$(D_m)_A = (D_m)_B \quad (2)$$

These assumptions are valid provided the coagulation process does not appreciably increase the particle size. The first assumption is actually valid to better than 20% regardless of particle size for $$\alpha > 1$$

where $\alpha$ is the size parameter defined by $$\alpha = \pi D_p / \beta$$

and $\beta$ is the wavelength at incident light. The accuracy is greatly improved when the change in diameter is small. The second assumption is derived from the fact that the diameter of average mass changes much more slowly than does the number concentration. For example, a factor of 2 concentration change only results in a 25% change in $D_m$. Therefore, the transit time between cells should be sufficiently short to allow less than a factor of 2 change in concentration. Using $D_m$ to describe the particle size and not the geometric size will ensure the stability of the particle size.

Using assumptions (1) and (2), and dividing equation (3b) by equation (3a), the following equation is obtained:

$$\frac{\ln[I_B/(I_O)_B]}{\ln[I_A/(I_O)_A]} = \frac{L_2 N_B}{L_1 N_A} \quad (4)$$

This equation is dependent only on the measured values of the intensity ratios for each cell and the number concentration in each cell. Physically, a series cell extinction monitor will measure the decrease in extinction due to the coagulation process reducing the total cross sectional surface area of aerosols.

The difference in number concentration is assumed to be a result of only the coagulation process. As a result, the change in number concentration as a function of time for a system of aerosols undergoing coagulation is can be determined according to W. A. Fuchs, in *The Mechanics of Aerosols*, Pergamon Press, New York, N.Y., pp 288–290, (1964)

$$dN/dt = 4\pi D_p D N^2 [1 + D_p (\pi D t)^{-\frac{1}{2}}] \quad (5)$$

where

D = diffusion coefficient for particle of diameter $D_p$ (cm²/s), and t = coagulation time (s).

Depending on experimental conditions, the second term in the bracket is usually less than 1 and considered negligible. The solution to the simplified form of Equation (5) is given by $$1/N_O = 1/N - kt \quad (6)$$

where $N_O$ = initial number concentration (cm$^{-3}$)
$N$ = number concentration after time t (cm$^{-3}$)
$k$ = coagulation coefficient (cm$^3$/s).

The coagulation coefficient can be calculated for monodisperse particles of given size by $$k = 4BTC/3h \tag{7}$$

where
B = Boltzman's constant
T = temperature (K)
C = Cunningham slip correction factor, and
h = gas viscosity (g/cm-sec).

Based on the work of T. Gillespie in "The Effect of Size Distribution on the Rate Constants for Collisions in Disperse Systems," *J. Colloid Science*, 18:562 (1963) and P. C. Riest in *Introduction to Aerosol Science*, MacMillan Publishing Co., New York, N.Y., p. 259 (1984), the following expression for the coagulation coefficient of log-normally distributed polydisperse aerosols can be stated $$k = 2BT[1 + \exp(\ln^2 GSD) + 4.52[\exp(0.5 \ln^2 GSD) + \exp(2.5 \ln^2 GSD)]g/D_p]3h. \tag{8}$$

where
GSD = geometric standard deviation of the distribution
g = mean free path of the gas molecules (cm).

The difference between the coagulation coefficients calculated by Equations (7) and (8) is less than 15 percent when $g/D_p < 0.02$ and GSD < 1.5. Changing from monodisperse to polydisperse aerosols does not significantly alter Equation (6).

In terms of the dual cell light extinction aerosol monitor, Equation (5) can be written with the initial concentration equal to the number concentration in the first cell, $N_A$, and the final concentration equal to the number concentration in the second cell, $N_B$.

$$N_A/N_B = 1 + ktN_A \tag{9}$$

Substituting into Equation (4) yields $$\frac{L_2 \ln[I_A/(I_0)_A]}{L_1 \ln[I_B/(I_0)_B]} = 1 + ktN_A \tag{10}$$

In Equation (9), the path lengths are known, the intensity ratios are directly measured and the transit time is determined from the volume between cells and the volumetric flow rate. This leaves two unknowns, the number concentration, which is the desired result and the coagulation coefficient which depends on particle size through the slip correction factor. To effectively use Equation (10), one must either have independent knowledge of the particle size so that k can be calculated, or operate the extinction cells at conditions such that k remains constant. At STP conditions this occurs for particle sizes greater than about 5 μm. However, for high temperature and high pressure operating conditions, the minimum particle size above which the coagulation coefficient can be considered constant, decreases rapidly. For example, at pressures of 7 MPa and temperatures of 640K, which are typical of simulated nuclear reactor accidents, k can be considered constant for particle sizes as low as 0.1 μm. As long as k can be considered a known constant, then a dual cell light extinction device can directly measure the number concentration of an aerosol according to Equation (10).

Figure 2:
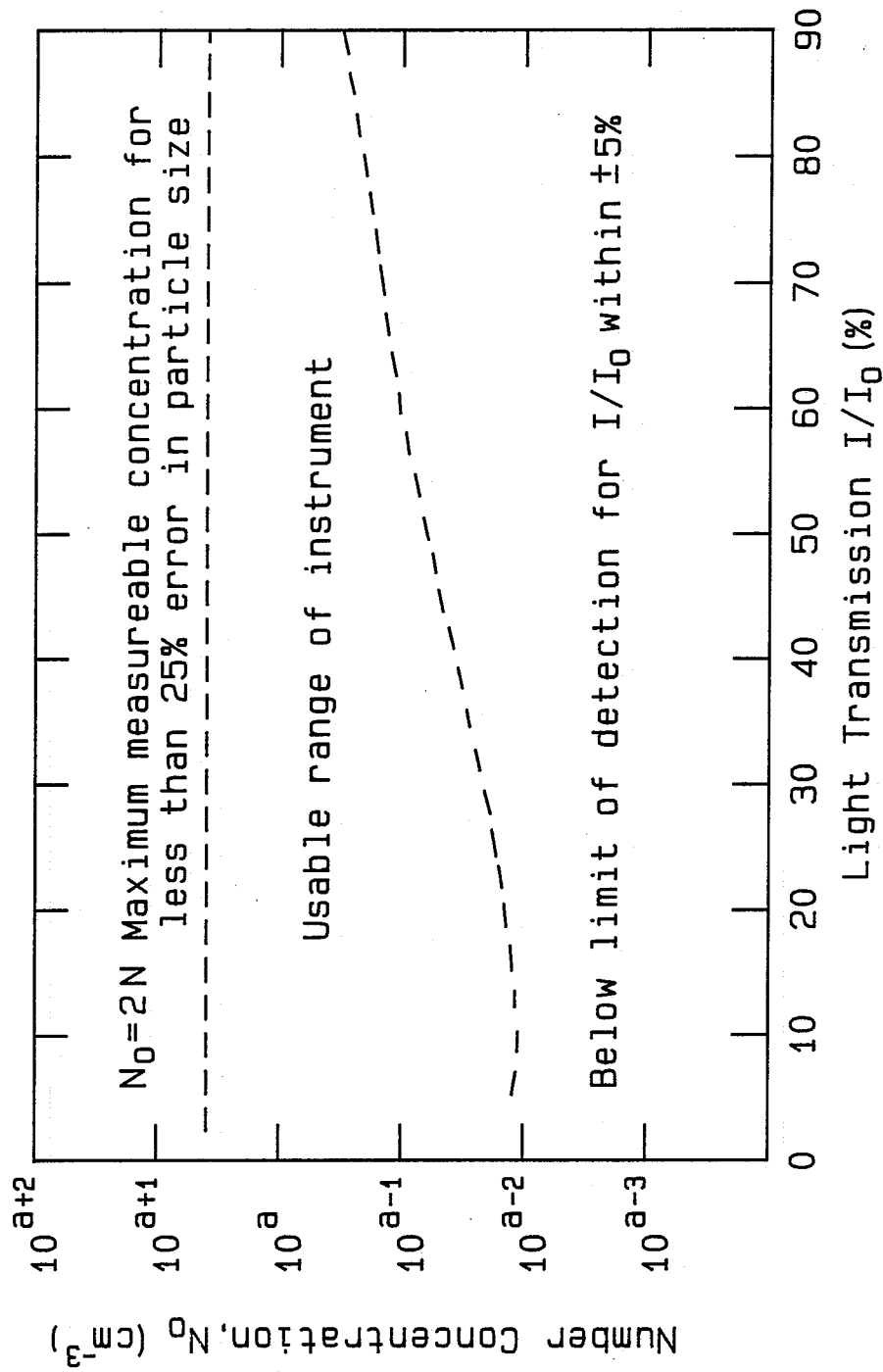
FIG. 2 is a graph plotting number concentration verses light transmission.

The dual light cell monitor can be used to determine the number concentration using the data shown in FIG. 2. To use FIG. 2, the coagulation coefficient k, must be known and nearly constant between the cells. The flow rate through the device must be known and an estimate to within an order of magnitude or two of the number concentration is necessary. The transit time, T, can then be calculated according to $$\text{Log } N = \pm x + \log(1/kT)$$

where x is a design factor determined by the order of magnitude uncertainty in N. Given the flow rate, transit time and path length, the separation distance between cells can be determined. Note that the ability to vary the flow rate will extend the range of measurable concentrations.

Figure 3:
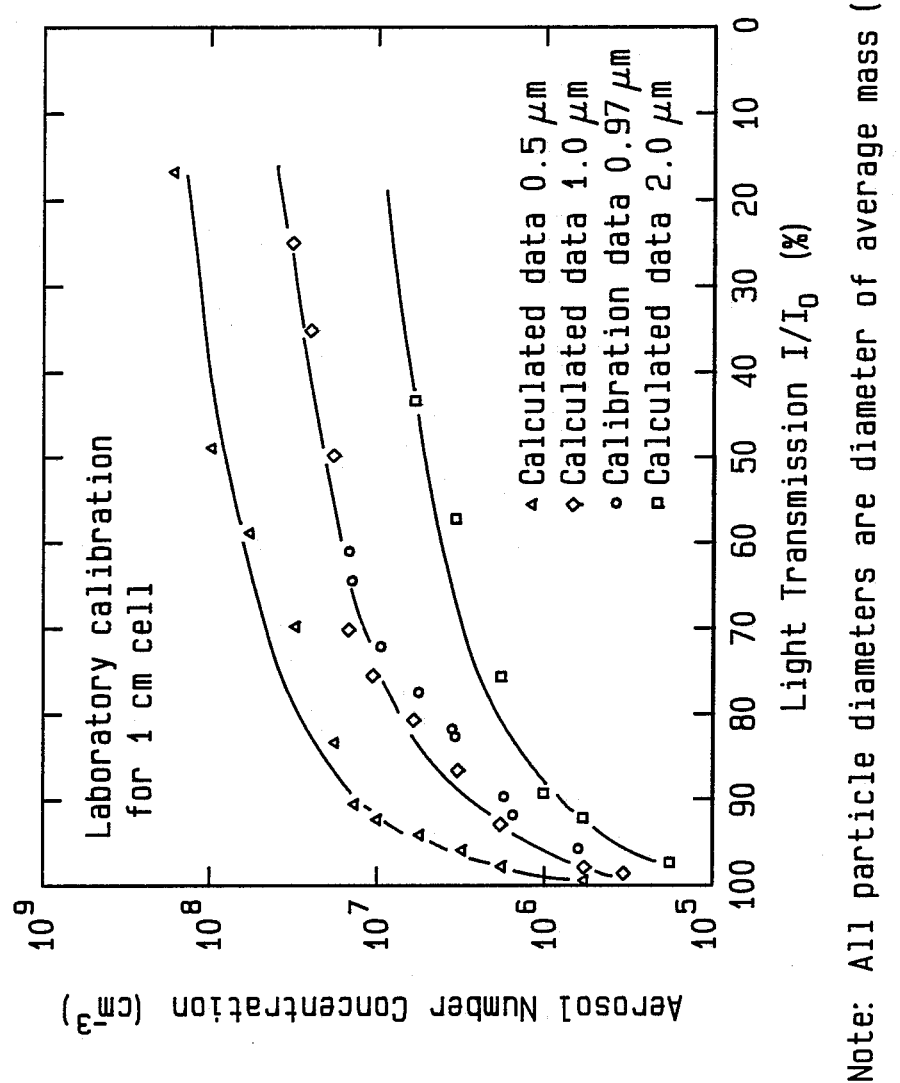
FIG. 3 is a graph plotting aerosol number concentration verses light transmission for a first cell.

The path lengths of the cells should be designed to provide intensity ratios less than 60%. The reason for choosing intensity ratios less than 60% can be deduced by examining FIGS. 3 and 4. These figures are the result of both calculations and experimental measurements for two individual cells with path lengths of 1 cm and 4 cm. From the shape of the curves, it is clear that only those regions of the curve where a small change in number concentration results in a large change in intensity ratio, will produce the desired instrument response. If the device is operated in a region where large concentration changes produce little intensity change, then reasonable estimates of the number concentration become impossible. This factor is inherent in the shape of the lower curve in FIG. 2. Higher extinction values provide greater instrument response.

The lower curve in FIG. 2 was generated assuming that the measured value of $I/I_0$ was only good to within 5%. This error limit is based on the results of FIGS. 3 and 4. The middle curve in each figure compares the experimental values of extinction with calculated values. The experimental values were determined by measuring the extinction for various number concentrations of ammonium chloride generated by the combination of ammonium hydroxide and hydrochloric acid vapors. Number concentrations were calculated based on the mass collected and the size distribution measured by a cascade impactor. The calculations assumed a similar size distribution of white non-absorbing spheres. The differences between calculated and measured extinction are less than 4%. This lower limit to the usable range of a dual cell extinction device is due to insufficient change in intensity and hence insufficient coagulation.

A fixed change or uncertainty in the intensity ratio requires a much larger change in number concentration as the value of the intensity ratio approaches 100%. For a fixed value of kt, a larger change in number concentration requires a larger initial number concentration. Therefore, the minimum detectable number concentration increases as the intensity ratio increases. Lower particle concentrations can be measured by increasing the path length of the light beams and increasing the coagulation time between cells. Higher concentrations can be measured by reducing the coagulation time between cells. The lower limit cannot be made arbitrarily small since it depends on the uncertainly in the system, including particle loss mechanisms, stability of the light source, quality of the optics and noise in the electronics.

The upper curve defining the viable range of a dual cell light extinction device is based on the previous discussion that assumes the diameter of average mass remains constant. It was assumed for illustrative purposes that the maximum allowable change in $D_m$ be restricted to less than 25%. This error when combined with other possible errors such as the slip correction uncertainty, and the error in $Q_{ext}$, would result in a total maximum uncertainty of less than 35%. This upper limit is then solely a function of a too rapid coagulation process for the device, resulting in the invalidation of the constant $D_m$ assumption.

Figure 5:
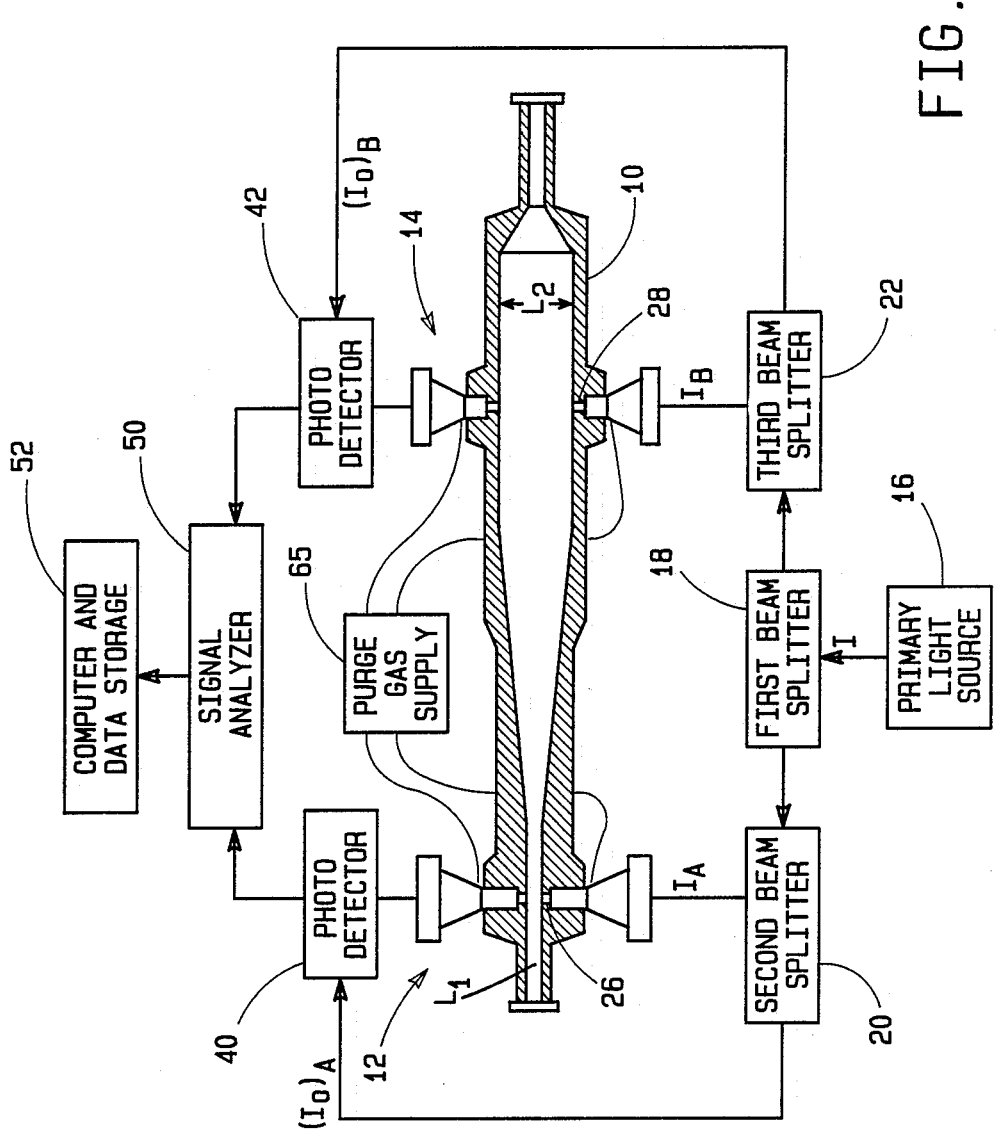
FIG. 5 is a detailed schematic of the present invention.

Referring to FIG. 5, there is depicted a gasflow chamber 10 through which can flow the gas the aerosol number of which can be determined by the present invention. This chamber can be located in an emissions stack through which the gas flows or may be in a shunt through which only a representative sample portion of the gas flows. In this embodiment, the gasflow chamber is located in a sampling shunt.

A primary light source 16 provides light for use in the present invention. Primary light source 16 in the present embodiment is a light emitting diode (LED) with an output wavelength between 810–890 nm. Light beam, I, from primary light source 16 is mechanically chopped and focused onto an optical fiber and then conveyed by optic fiber to first beam splitter 18. First beam splitter 18 splits light beam I into light beams $I_A$ and $I_B$. Beams $I_A$ and $I_B$ are directed by optic fiber to second beam splitter 20 and third beam splitter 22, respectively. Second beam splitter 20 splits out part of beam $I_A$ into beam $(I_O)_A$ which will serve as a reference to monitor the stability of the LED output. The third beam splitter 22 breaks out part of beam $I_B$ as $(I_{OB}$ for the same purpose. Beams $I_A$ and $I_B$ are conveyed by optic fiber through windows 26 and 28, respectively, that allow beams $I_A$ and $I_B$ to enter the interior of gasflow chamber 10. Beams $I_A$ and $I_B$ pass across the gasflow chamber 10 and collected are collected on optic fibers in light cells 12 and 14, respectively. These signals, modified by the extinction due to aerosols in the gap, are conveyed to first detector 40 and second detector 42, respectively. These detectors may be silicon photodiode detectors. First detector 40 and second detector 42 also receive the reference signals $(I_O)_A$ and $(I_O)_B$ from second beam splitter 20 and third beam splitter 22, respectively. Output of first detector 40 and second detector 42 is $(I/I_O)_A$ and $(I/I_O)_B$, respectively. These signal beams $(I/I_O)_A$ and $(I/I_O)_B$ are conveyed to signal analyzer 50 where the signal is then demodulated by a phase-lock amplifier 50 and relayed to a computer 52 which may include a means for data storage. Computer 52 may be programmed to calculate the number concentration automatically and display the results on a monitor. Alternately, the data may be stored in computer 52 for later analysis or sent to other computers that monitor the entire system.

Figure 6:
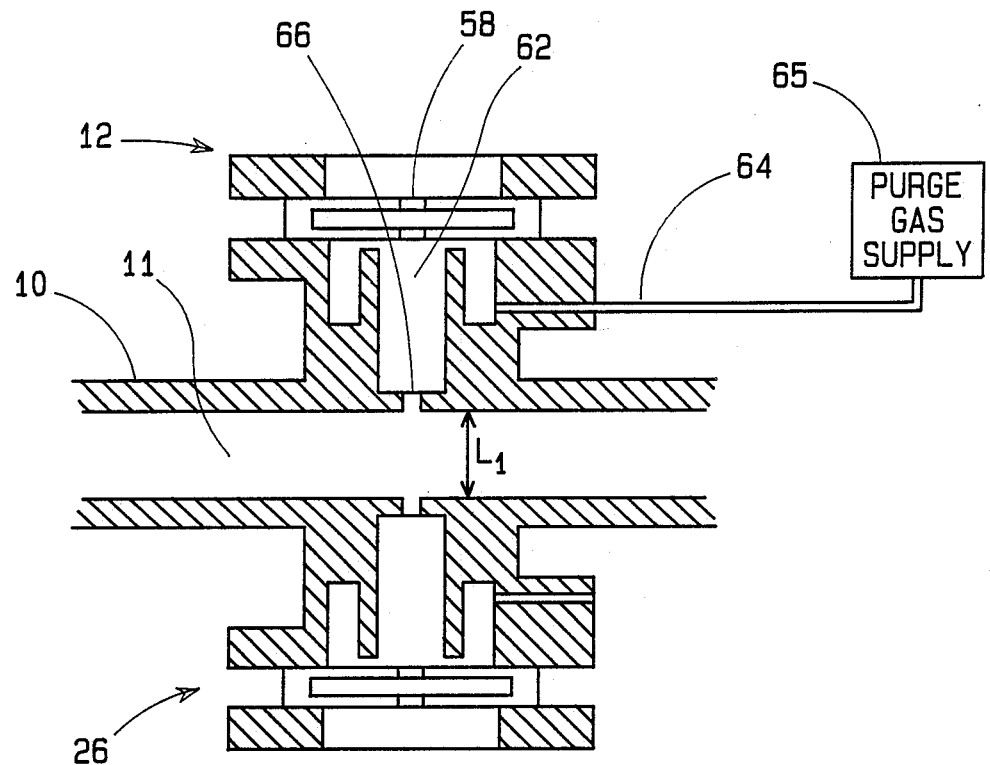
FIG. 6 is a cutaway a section of a light cell and part of the gasflow chamber.
Figure 7:
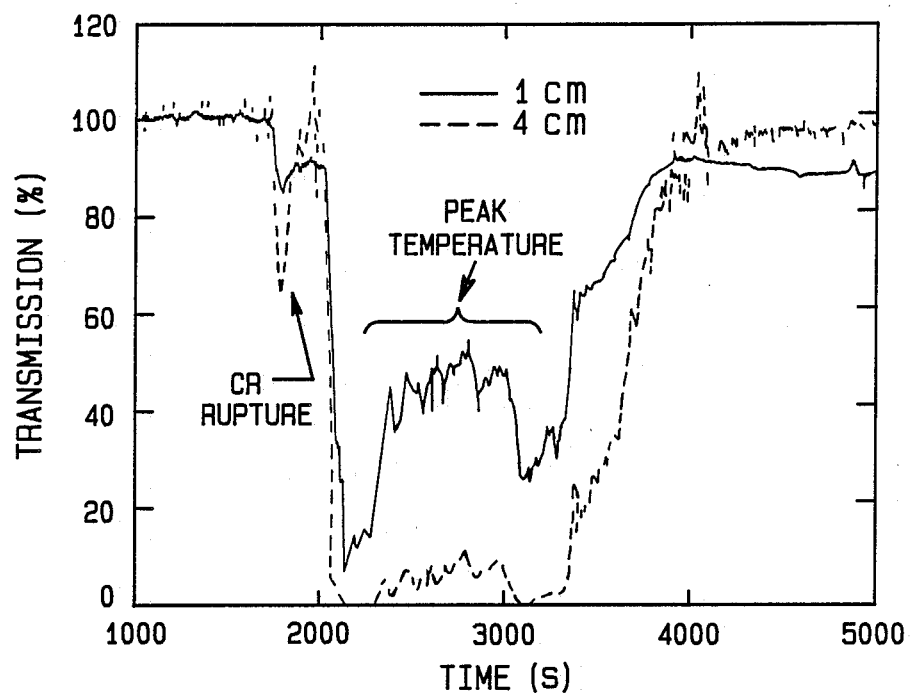
FIG. 7 is a graph plotting transmission verses time.

Referring to FIG. 6, there is depicted a cutaway view of light cell 12. (Light cell 14 has a similar construction except for the optical length across the chamber). Light cell 12 includes spinel window 58 constructed to handle the high temperatures (644K) and high pressures (7 MPa) encountered for this application. As used in this embodiment for the reactor core experiment, the entire sampling shunt line, including the gasflow chamber 10 and associated measurement equipment, was heat traced in order to maintain isothermal conditions at 644K. Heat tracing was necessary to prevent additional vapor condensation onto the aerosols and to prevent thermophoretic losses by the aerosols.

Spinel window 58 is located behind purge chamber 62 through which a small flow of clean gas can enter via gas inlet 64 to minimize aerosol deposition on the window. Purge gas is provided by gas supply 65. Spinel window 58 is directly across purge chamber 62 from pinhole orifice 66 that opens to gasflow chamber 10. Windows 26 and 28 can also include a means for maintaining the window clear, such as the purge gas supply. Purge gas supply 68 provides gas to cells 12 and 14 and windows 26 and 28, as depicted in FIG. 5.

The receiving optics are designed so that multiple scattering effects would be minimized. The pinhole orifice 66 and spinel window 58 and the receiving fiber act as a light collimator, eliminating any stray or multiply-scattered light. The geometry of the receiving optics allow about a six degree cone of light to be passed through the pinhole and impinge on the receiving fiber. This geometry meets with the first part of the Hodkinson criterion described by C. N. Davies, in *Aerosol Science*, Academic Press, New York, N.Y., pp. 294–297 (1966) that requires the acceptance angle of light to be less than $0.38\beta/\pi D_P$, where $\beta$ is the wave length of the incident light. Based on the parameter for this usage, the restriction is met for a six degree acceptance angle where the geometric particle size, $D_P$ is less than 1 $\mu$m. The second part of the criterion indicates that multiple scattering can be a problem only when the distance between particles is less than a few particle diameters. Assuming five particle diameters constitutes "a few", calculations indicate that more than $10^{10}$ particles/cm$^3$ of 1 $\mu$m diameter are required to cause sufficient multiple scattering errors to invalidate the Lambert-Beer equation. Again, for this embodiment, the expected number concentrations were always significantly below $10^{10}$ particles/cm$^3$.

As mentioned above, in the present embodiment the cells have different optical path lengths, For the first cell, $L_1 = 1$ cm, and for the second cell, $L_2 = 4$ cm. The use of cells with different path lengths resulted from the adaptation of this invention to an existing system. A design such as this utilizing different path lengths provides a wide range of extinction measurement capability which can be particularly useful where no "a priori" information is available concerning the number concentration and particle diameter of aerosols expected. However, the present invention is equally applicable to use with an aerosol gasflow chamber having light extinction cells of identical path lengths and in fact the calculation of number concentration is thereby somewhat simplified.

In the present embodiment, the change in the LED output during the experiment was less than 0.1 percent. Extinction was measured as the ratio of the amount of light reaching the detector after passing through the aerosol to the initial intensity with no aerosols in the cell. Data on the intensity ratio for each cell was acquired every three seconds. The results for the SFD 1-4 test are shown in the intensity ratios versus time spectrum in FIG. 6. The flow rate through the monitor was variable but was measured and recorded every three seconds. The volume between the cells was 233.9 cm$^3$. The pressure was a constant 6.9 MPa, and the temperature of the sampling line was heat traced to 644K. The transit time between cells varied from 4 to 12 seconds, averaging about 6 seconds.

Figure 4:
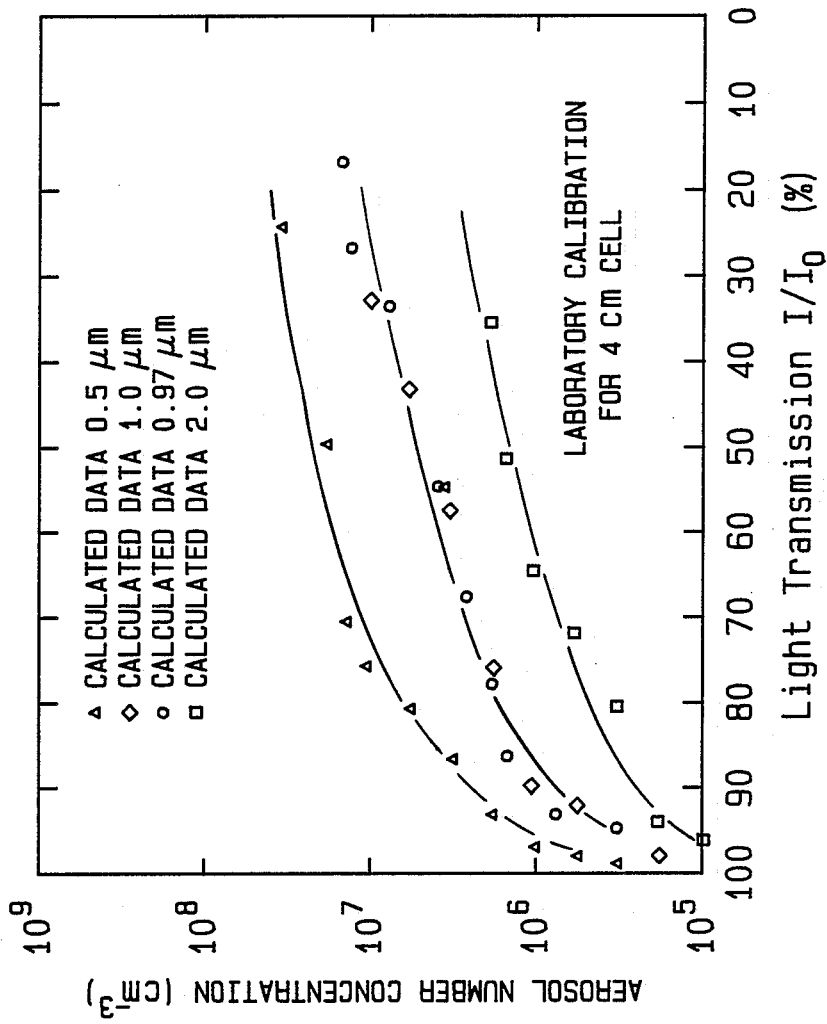
FIG. 4 is graph plotting aerosol number concentration verses light transmission for a second cell.

After correcting for the difference in path lengths, the intensity ratio from the FIG. 4 data, is less for the 4 cm cell as compared to the 1 cm cell. This decrease in extinction is expected to be due to coagulation reducing the number concentration at the second cell. There are other loss mechanisms that may cause this decrease, but calculations using the experimental parameters indicate that the differential losses due to diffusion or settling are less than 0.1 percent for time scales on the order of the transit time between cells. On the other hand, for sufficiently high number concentrations, coagulation theory, as previously described, can easily explain the detected differences and provide a measure of the aerosol number concentration as a function of time.

Figure 8:
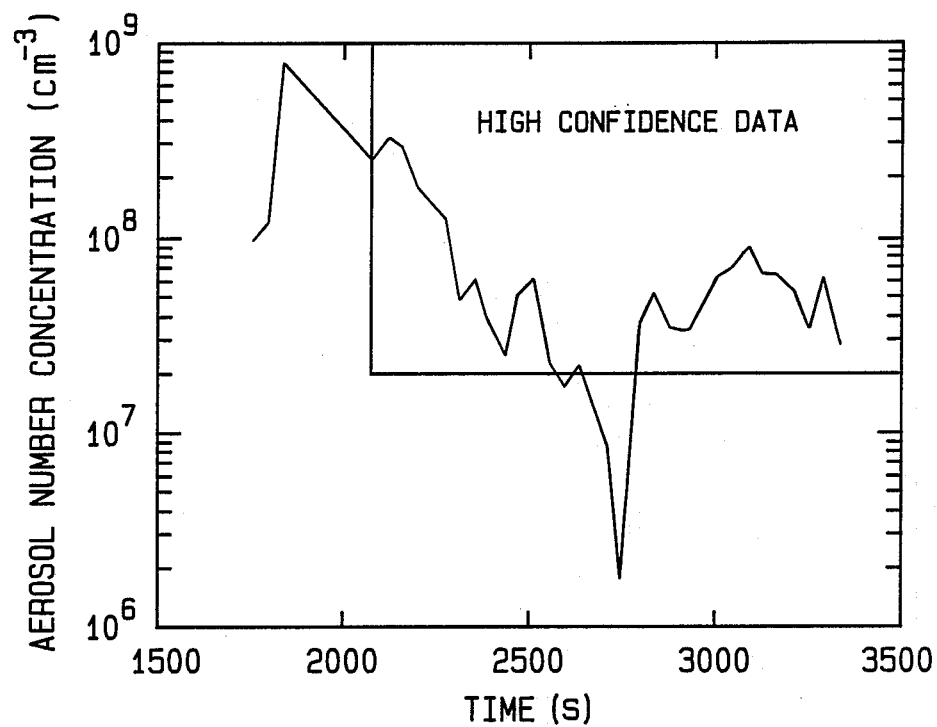
FIG. 8 is a graph plotting aerosol concentration verses time.

In addition to the use of the present invention to determine the aerosol number, the present invention also can be used to determine the particle number concentration and estimates for particle size and mass concentrations. By way of example, consider the application of Equation (8) to the experimental data for the PBF SFD 1-4 test. The intensity ratio measurements were corrected for the observed change in reference intensity possibly caused by thermal or radiation degradation or aerosol deposition on the windows. The first step is to determine the behavior of the coagulation coefficient, k. Calculations indicate that the slip correction factor does not vary by more than 5 percent for particles greater than 0.1 $\mu$m in size for the SFD 1-4 experimental conditions. This result implies that the coagulation coefficients for particles greater than 0.1 $\mu$m are equal. The only variation from a constant value for k is due to the gas composition change from argon and steam to argon and hydrogen for the PBF experiment. The variation in viscosity would cause a variation in coagulation coefficient of less than 20 percent. The average value of k is calculated to be $4.2 \cdot 10^{-10}$ cm$^3$/s. Previous similar experiments and the results from aerosol computer codes that consider condensation and coagulation indicate the expected mean particle size is greater than 0.1 $\mu$m and probably fluctuates around 0.5 $\mu$m. Because the intensity ratios and flow rates, hence transit times, are measured and k is nearly constant, the number concentration can then be calculated according to Equation (8). The results are presented in FIG. 8.

The area of the curve labeled "high confidence region," indicates that the number concentration is accurate to within better than ±25 percent, based on the total uncertainty in k, $D_m$, the slip correction and on calibration data. The calculated lower limit indicates that for an intensity ratio less than 60%, the number concentration must be greater than $3.0 \cdot 10^7$ cm$^{-3}$. The high particle concentration limit is based on the number of particles required for a given k and transit time, determined from experimental conditions, to permit coagulation to increase the particle size by 10 percent. The area outside of the high confidence region has a probable error of greater than ±25 percent. These areas have either particle concentrations fewer than $3 \cdot 10^7$ cm$^{-3}$ or greater than $10^9$ cm$^3$. The majority of the uncertainty in the PBF 1-4 measurement is caused by the variable gas composition. If the gas composition were fixed, the viscosity would be known exactly and the coagulation coefficient would be known more precisely.

The remaining information about the aerosol distribution as a function of time in the SFD 1-4 test can be extracted by using the derived number concentration in conjunction with an independent measurement of the particle size distribution at a given period of time during the experiment. This method will allow the particle size and mass concentrations to be estimated as a function of time.

Information independent of the PBF aerosol monitor was obtained by collecting a portion of the aerosol stream on filters immediately after the monitor. Particles were collected on six individual filters, each filter sampling the aerosol stream for 60 seconds at different times during the test. Unfortunately, only filter six collected a low enough area density of particles to allow the use of an automated particle counter on the scanning electron microscope (SEM) photographs. The other five filters were loaded with so many layers of particles that it was impossible to determine the size of individual clusters as they existed in the aerosol stream prior to collection. The data collected from filter six was used to determine the number mean particle size and geometric standard deviation of the distribution of particles collected from 3060 to 3120 seconds. Based on the measured distribution parameters, the diameter of average mass was calculated. The diameter of average mass is again assumed to always be constant between the monitor and the filter.

Since the number concentration, intensity, ratio, path length and particle size are known or assumed, the integral value of the extinction coefficient $Q_{ext}$, can be calculated by substituting into Equation (3a) the value of the mean particle diameter, the number concentration from Equation (10), and the average intensity ratio measured by the aerosol monitor while filter six was collecting particles. The intensity ratios are known and number concentrations have been calculated as a function of time. If the assumption is made that $Q_{ext}$, calculated for one time period, can be applied over the entire duration of the experiment, in other words the value of $Q_{ext}$ is assumed to always be a constant, then Equation (3a) enables the diameter of average mass to be calculated for any period of time during the experiment. However, the particle size throughout the test is certainly not constant so the value of $Q_{ext}$ can be expected to have an error of about 20% for $\alpha > 1$. In addition, the nature of a severe fuel damage experiment causes the particle composition to change as a function of time due to changes in temperature, gas composition, chemical reactions, and pressure. These processes result in a time variable index of refraction and, hence, a variable extinction coefficient. Therefore, the best that can be done to estimate the particle size as a function of time, is to estimate the bounds that contain the probable particle size.

Figure 9:
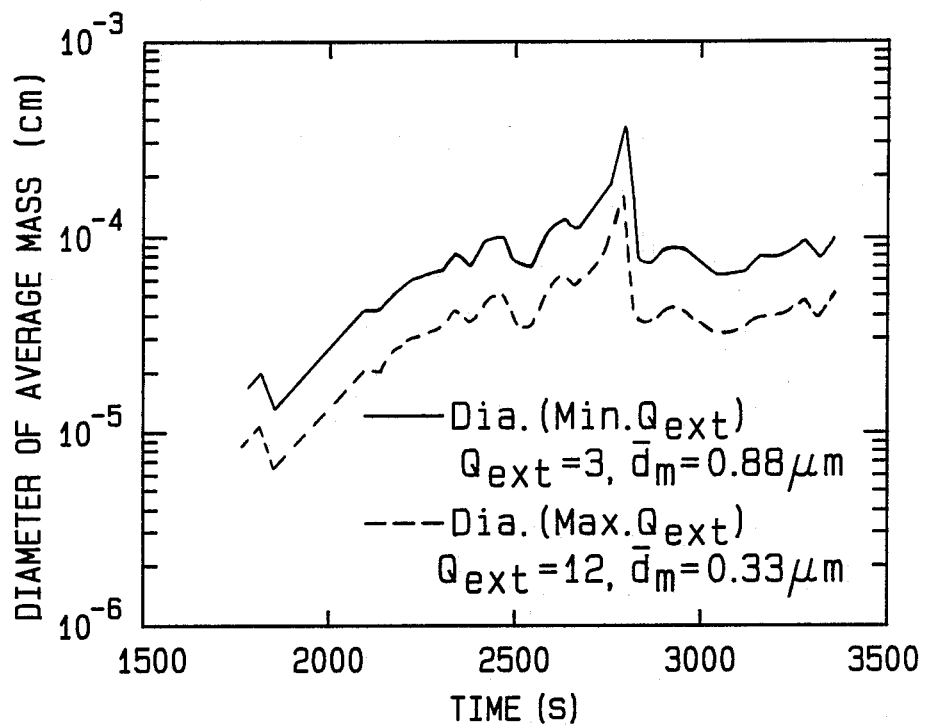
FIG. 9 is a graph plotting diameter of average mass verses time.
Figure 10:
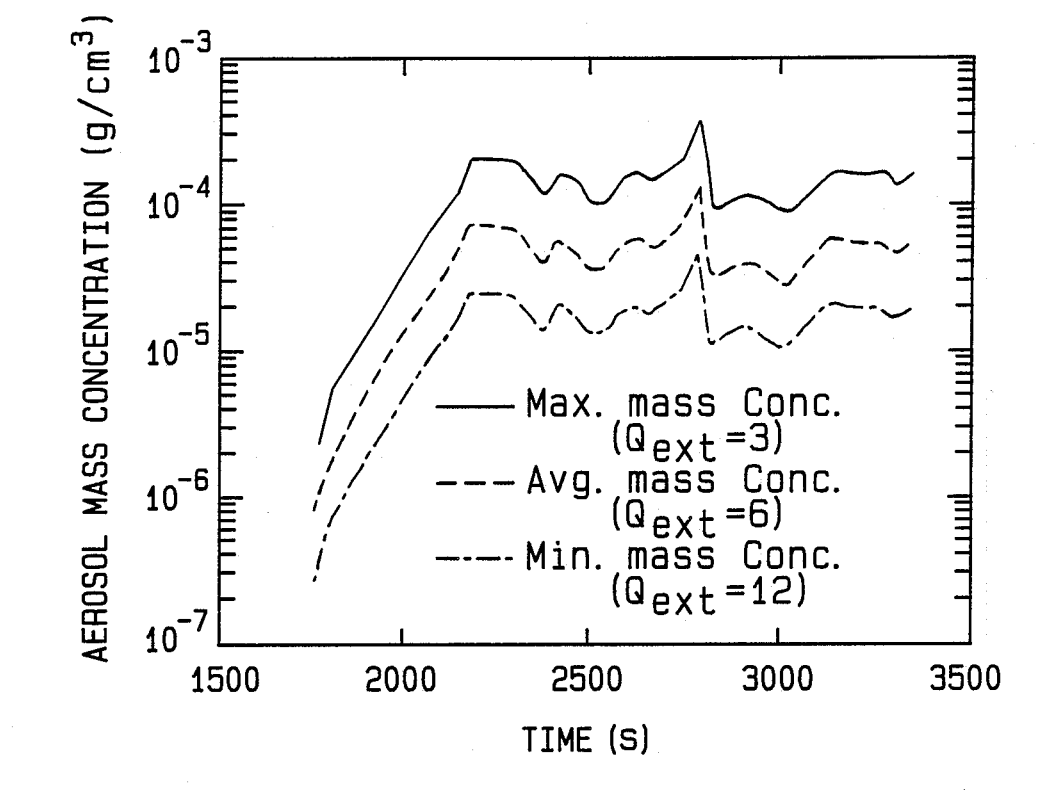
Figure 11:
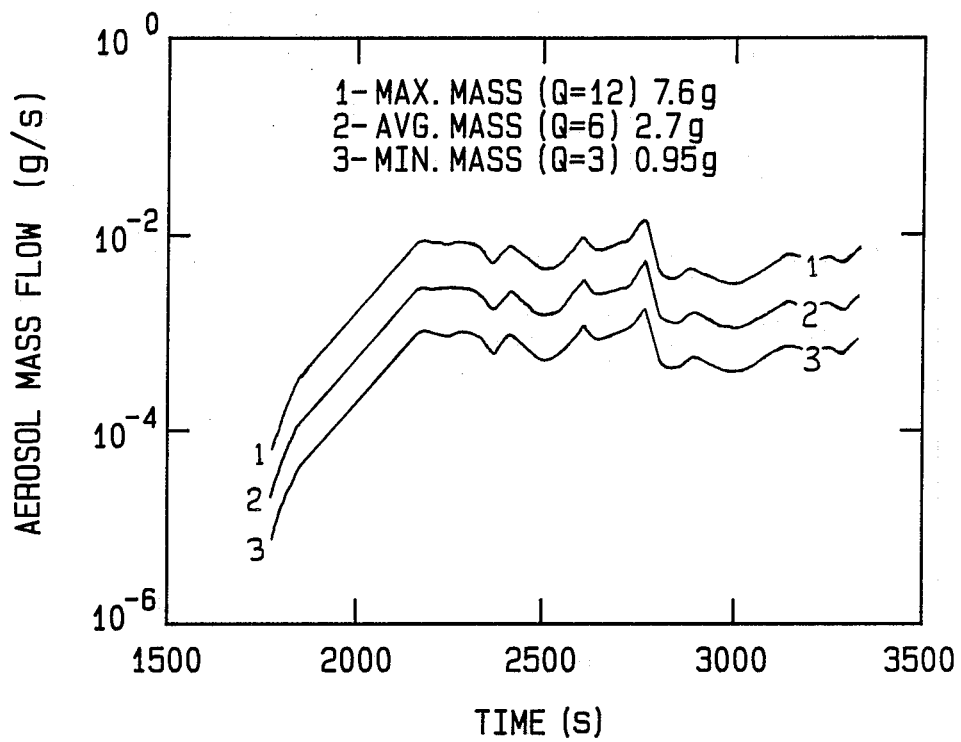
FIG. 11 is a graph plotting aerosol mass flow verses time, cutaway of one section of the gasflow chamber and includes cutaway detail of one of the light cells.

In *Light Scattering by Small Particles* by H. C. Van de Hulst, Dover Publications, New York, N.Y., pp. 267-292 (1981) and *Handbook on Aerosols,* by R. Dennis, Technical Information Center, Office of Public Affairs, U.S. Energy Research and Development Administration, Oak Ridge, Tenn., pp. 66-92 (1976), it is indicated that for most metallic or metal oxide particles, which are most likely to be formed in a severe fuel damage test, the differences in extinction coefficients are probably less than a factor of two. Also, based on the number concentrations and the transit times involved, the particle size increase is probably less than a factor of the square root of 2. Combining these uncertainties results in the estimate for the bounds on the particle size. Allowing the value of the exponent in Equation (3a) to vary between twice as large and half as large, yields a bound of approximately one sigma for the calculated particle size data. This data is graphically presented in FIG. 9. Using the number concentration, particle size, and flow rate information and assuming a particle density of 10 g/cc, the estimates bounding the aerosol mass concentration and mass flow rate can be obtained as in FIGS. 10 and 11. Finally, integrating FIG. 11 gives limits on the total aerosol mass that passed by the aerosol monitor during the experiment. The measured total mass based on these assumptions lies in the range of 1 to 7 grams, with the most likely value being about 2.5 grams.

In general, a series cell light extinction monitor can provide real time number concentration measurements to within an accuracy of better than 30% over a range of two and one-half orders of magnitude decreasing to one order of magnitude for lower extinction values. As described above, additional assumptions and information allow the invention to be able to estimate the time dependent functions of particle size, aerosol mass concentration, and aerosol mass flow rate. The information provided by this invention has enabled the most accurate determination to date, for a severe fuel damage test, of the number concentration, particle size distribution, and aerosol mass flux as a function of time.

The present invention has applicability to other situations involving high particle concentrations. The method is especially well suited for measuring high number concentrations of particles, in-situ, as a function of time for high temperature, high pressure experiments.

The embodiments of the invention in which an exclusive property or privilege is claimed are defined as follows:

1. A device for determining number concentration of an aerosol comprising:

a chamber capable of conveying the aerosol with a known gas volumetric flow rate, a primary light source capable of providing light to the interior of said chamber at a first location and at a second location separated from the first location, a first light detector cell capable of measuring the extinction of light across said chamber from the first location, a second light detector cell capable of measuring the extinction of light across said chamber from the second location, whereby the number concentration of the aerosol can be determined in accordance with the formula $$\frac{L_2 \ln[I_A/(I_0)_A]}{L_1 \ln[I_B/(I_0)_B]} = 1 + ktN_A$$

where $L_1$ is the path length of a light beam across said chamber from said light source to said first light extinction cell, $I_A$ is the transmitted light intensity measured through the aerosol at said first light extinction cell, $(I_O)_A$ is the transmitted light intensity measured at said first light extinction cell without the aerosol, $L_2$ is the path length of a light beam across said chamber from the light source to said second light extinction cell, $I_B$ is the transmitted light intensity measured through the aerosol at said second light extinction cell, $(I_O)_B$ is the transmitted light intensity measured at said second light extinction cell without the aerosol, k is the coagulation coefficient ($cm^3/s$), t is the coagulation time (s), and $N_A$ is the number concentration at the first light extinction cell ($cm^{-3}$).

2. The device of claim 1 including a signal analyzer coupled to outputs of said first light detector cell and the output of said second light detector cell.

3. The device of claim 2 including a first photo detector coupling said first light extinction cell and said signal analyzer, said first photo detector capable of converting an optical signal from said first light extinction cell into an electrical signal, and a second photo detector coupling said second light extinction cell and said signal analyzer, said second photo detector capable of converting an optical signal from said second light extinction cell into an electrical signal.

4. The device of claim 3 including a computer means coupled to said signal analyzer, said computer means capable of storing data from said signal analyzer.

5. The device of claim 4 in which said computer means is further capable of calculating the number concentration of an aerosol conveyed in said gasflow chamber.

6. The device of claim 5 including:

a first beam splitter responsive to a light beam from said primary light source, said first beam splitter capable of splitting a light beam from said primary light source into a beam directed to said chamber at the first location and a beam directed to said chamber at the second location.

7. The device of claim 6 including:

a second beam splitter responsive to a light beam from said first beam splitter, said second beam splitter capable of splitting a light beam from said first beam splitter into a beam directed to said chamber at the first location and a reference beam directed to the first photo detector, and a third beam splitter responsive to a light beam from said first beam splitter, said third beam splitter capable of splitting a light beam from said first beam splitter into a beam directed to said chamber at the second location and a reference beam directed to the second photo detector.

8. The device of claim 7 including a purge gas supply connected to said first light extinction cell and said second light extinction cell, said purge gas supply capable of providing a gas to clean said first light extinction cell and said second light extinction cell.

9. The device of claim 8 in which said first light extinction cell includes:

a first pinhole orifice opening to said chamber across from the first location, a first purge gas chamber connected to said gasflow chamber by said first pinhole orifice, a first gas supply inlet connecting said gas supply to said first purge gas chamber, and a first spinel window directly opposite said first purge gas chamber from said first pinhole orifice.

10. The device of claim 9 in which said second light extinction cell includes:

a second pinhole orifice opening to said chamber across from the second location, a second purge gas chamber connected to said gasflow chamber by said second pinhole orifice, a second gas supply inlet connecting said gas supply to said second purge gas chamber, and a second spinel window directly opposite said second purge gas chamber from said second pinhole orifice.

11. A method for determining the number concentration of a aerosol flowing in a gasflow chamber where the gas volumetric flow rate is known comprising the steps of:
sending a light beam across the gasflow chamber at a first location in the gasflow chamber,
measuring the light extinction in a first light extinction cell across the gasflow chamber from the first location,
sending a light beam across the gasflow chamber at a second location in the gasflow chamber the second location being separated from the first location by a known volume,
measuring the light extinction across the gasflow chamber in a second light extinction cell across the gasflow chamber from at the second location along the chamber whereby the number concentration of the aerosol can be determined by the formula $$\frac{L_2 \ln[I_A/(I_0)_A]}{L_1 \ln[I_B/(I_0)_B]} = 1 + ktN_A$$

where
$L_1$ is the path length of a light beam across the gasflow chamber to said first light extinction cell,
$I_A$ is the transmitted light intensity measured through the aerosol at said first light extinction cell,
$(I_0)_A$ is the transmitted light intensity measured at said first light extinction cell without the aerosol,
$L_2$ is the path length of a light beam across the gasflow chamber to said second light extinction cell,
$I_B$ is the transmitted light intensity measured through the aerosol at said second light extinction cell,
$(I_0)_B$ is the transmitted light intensity measured at said second light extinction cell,
k is the coagulation coefficient (cm$^3$/s),
t is the coagulation time (s), and
$N_A$ is the number concentration at the first cell (cm$^{-3}$).

12. The method of claim 11 including the step of cleaning the first and second light extinction cells with a purge gas.

13. A method for estimating the aerosol mass concentration of an aerosol flowing in a gasflow chamber in which the gas volumetric flow rate is known comprising the steps of:
sending a light beam across the gasflow chamber at a first location along the gasflow chamber,
measuring the light extinction in a first light extinction cell across the gasflow chamber from the first location,
sending a light beam across the gasflow chamber at a second location along the gasflow chamber the second location being separated from the first location,
measuring the light extinction across the gasflow chamber in a second light extinction cell across the gasflow chamber from at the second location along the chamber, measuring the particle diameter of particles in the aerosol, measuring or estimating the particle density, whereby the aerosol mass concentration of the aerosol can be determined by the formula $$\frac{L_2 \ln[I_A/(I_0)_A]}{L_1 \ln[I_B/(I_0)_B]} = 1 + \frac{6ktm}{\pi D_m^3 p}$$

where
$L_1$ is the path length of a light beam across the gasflow chamber to said first light extinction cell,
$I_A$ is the transmitted light intensity measured through the aerosol at said first light extinction cell,
$(I_0)_A$ is the transmitted light intensity measured at said first light extinction cell without the aerosol,
$L_2$ is the path length of a light beam across the gasflow chamber to said second light extinction cell,
$I_B$ is the transmitted light intensity measured through the aerosol at said second light extinction cell,
$(I_0)_B$ is the transmitted light intensity measured at said second light extinction cell,
k is the coagulation coefficient (cm$^3$/s),
p is the particle density (g/cm$^3$)
t is the coagulation time (s), and
m is the aerosol mass concentration at the first light extinction cell (g/cm$^3$), and
$D_m$ is the particle diameter of average mass determined at one point in time (cm).

14. A method for estimating the aerosol mass flow rate of an aerosol flowing in a gasflow chamber comprising the steps of:
sending a light beam across the gasflow chamber at a first location along the gasflow chamber,
measuring the light extinction in a first light extinction cell across the gasflow chamber from the first location,
sending a light beam across the gasflow chamber at a $I_0$ second location along the gasflow chamber the second location being separated from the first location by a known volume,
measuring the light extinction across the gasflow chamber in a second light extinction cell across the gasflow chamber from at the second location along the chamber, measuring the particle diameter of particles in the aerosol, measuring or estimating particle density, whereby the aerosol mass concentration of the aerosol can be determined by the formula $$\frac{L_2 \ln[I_A/(I_0)_A]}{L_1 \ln[I_B/(I_0)_B]} = 1 + \frac{6ktm}{Q\pi D_m^3 p}$$

where
$L_1$ is the path length of a light beam across the gasflow chamber to said first light extinction cell,
$I_A$ is the transmitted light intensity measured through the aerosol at said first light extinction cell,
$(I_0)_A$ is the transmitted light intensity measured at said first light extinction cell without the aerosol,
$L_2$ is the path length of a light beam across the gasflow chamber to said second light extinction cell,
$I_B$ is the transmitted light intensity measured through the aerosol at said second light extinction cell,
$(I_0)_B$ is the transmitted light intensity measured at said second light extinction cell,
Q is the gas volumetric flow rate (cm$^3$/s),
k is the coagulation coefficient (cm$^3$/s),
p is the particle density (g/cm$^3$),
t is the coagulation time (s),
m is the aerosol mass flow rate through the first light extinction cell (g/s), and
$D_m$ is the particle diameter of average mass determined at one point in time (cm).

* * * * *